United States Patent [19]

Dobson et al.

[11] Patent Number: 5,564,415

[45] Date of Patent: Oct. 15, 1996

[54] HUMIDIFIER FOR A VENTILATOR

[75] Inventors: Darwin B. Dobson, Sun Prairie, Wis.;
Gregg D. Keefe, Boulder, Colo.;
Douglas R. Ogden, Arvada, Colo.;
Eugene P. Smith, III, Westminster, Colo.

[73] Assignee: Lifecare International, Inc., Westminster, Colo.

[21] Appl. No.: 472,328

[22] Filed: Jun. 7, 1995

[51] Int. Cl.$^6$ ............................................. A61M 16/16
[52] U.S. Cl. ........................... 128/204.14; 128/200.24; 220/308
[58] Field of Search ................ 261/119.1; 292/80, 292/81, DIG. 38; 220/308, 358; 128/204.14, 200.24, 203.16

[56] References Cited

U.S. PATENT DOCUMENTS

| | | | |
|---|---|---|---|
| 2,033,295 | 3/1936 | Parkin | 292/80 X |
| 3,064,853 | 11/1962 | Lents et al. | 220/358 |
| 3,100,485 | 8/1963 | Bartlett | 128/142 |
| 3,102,537 | 9/1963 | Bartlett | 128/142 |
| 3,225,758 | 12/1965 | Mörch | 128/29 |
| 3,477,609 | 11/1969 | Winkler, Jr. | 220/308 |
| 3,667,463 | 6/1972 | Barnes | 128/194 |
| 3,814,278 | 6/1974 | Beierle | 220/308 |
| 3,954,920 | 5/1976 | Heath | 261/104 |
| 4,026,285 | 5/1977 | Jackson | 128/192 |
| 4,086,305 | 4/1978 | Dobritz | 261/30 |
| 4,152,379 | 5/1979 | Suhr | 261/142 |
| 4,430,994 | 2/1984 | Clawson et al. | 128/203.27 |
| 4,588,425 | 5/1986 | Usry et al. | 128/200.21 X |
| 4,676,237 | 6/1987 | Wood et al. | 128/203.27 |
| 4,753,758 | 6/1988 | Miller | 261/139 |
| 4,832,012 | 5/1989 | Raabe et al. | 128/200.21 |
| 4,941,469 | 7/1990 | Adahan | 128/205.18 |
| 4,993,411 | 2/1991 | Callaway | 128/204.14 |
| 5,117,819 | 6/1992 | Servidio et al. | 128/204.18 |
| 5,148,801 | 9/1992 | Douwens et al. | 128/203.16 |
| 5,199,424 | 4/1993 | Sullivan et al. | 128/204.18 |
| 5,322,057 | 6/1994 | Raabe et al. | 128/203.12 |

FOREIGN PATENT DOCUMENTS

| | | | |
|---|---|---|---|
| 155768 | 12/1951 | Australia | 220/358 |
| 805033 | 11/1936 | France | 220/358 |
| 1010904 | 6/1952 | France . | |
| 124274 | 9/1900 | Germany | 128/204.14 |
| 867597 | 2/1953 | Germany . | |
| 195807 | 6/1967 | U.S.S.R. | 220/308 |
| 453690 | 9/1936 | United Kingdom | 220/358 |
| 1099252 | 1/1968 | United Kingdom | 220/358 |

*Primary Examiner*—V. Millin
*Assistant Examiner*—Eric P. Raciti
*Attorney, Agent, or Firm*—W. Scott Carson

[57] ABSTRACT

A sealing and retaining arrangement for a humidifier with separable top and bottom members and an attaching arrangement for rigidly connecting a ventilator or other respiratory device to the top of the humidifier in a predetermined, fixed position. The sealing and retaining arrangement is designed for use between separable top and bottom members of a humidifier. The top and bottom are made of relatively rigid material and have overlapping or telescoping portions with a flexible, resilient seal extending therebetween. The seal also serves to positively retain the top and bottom together while in use. The attaching arrangement is designed to rigidly connect the ventilator or other respiratory device to the top of the humidifier in a predetermined, fixed position. This is accomplished by rigidly coupling the air outlet of the ventilator directly to the air inlet of the humidifier without any intervening, flexible hose.

39 Claims, 9 Drawing Sheets

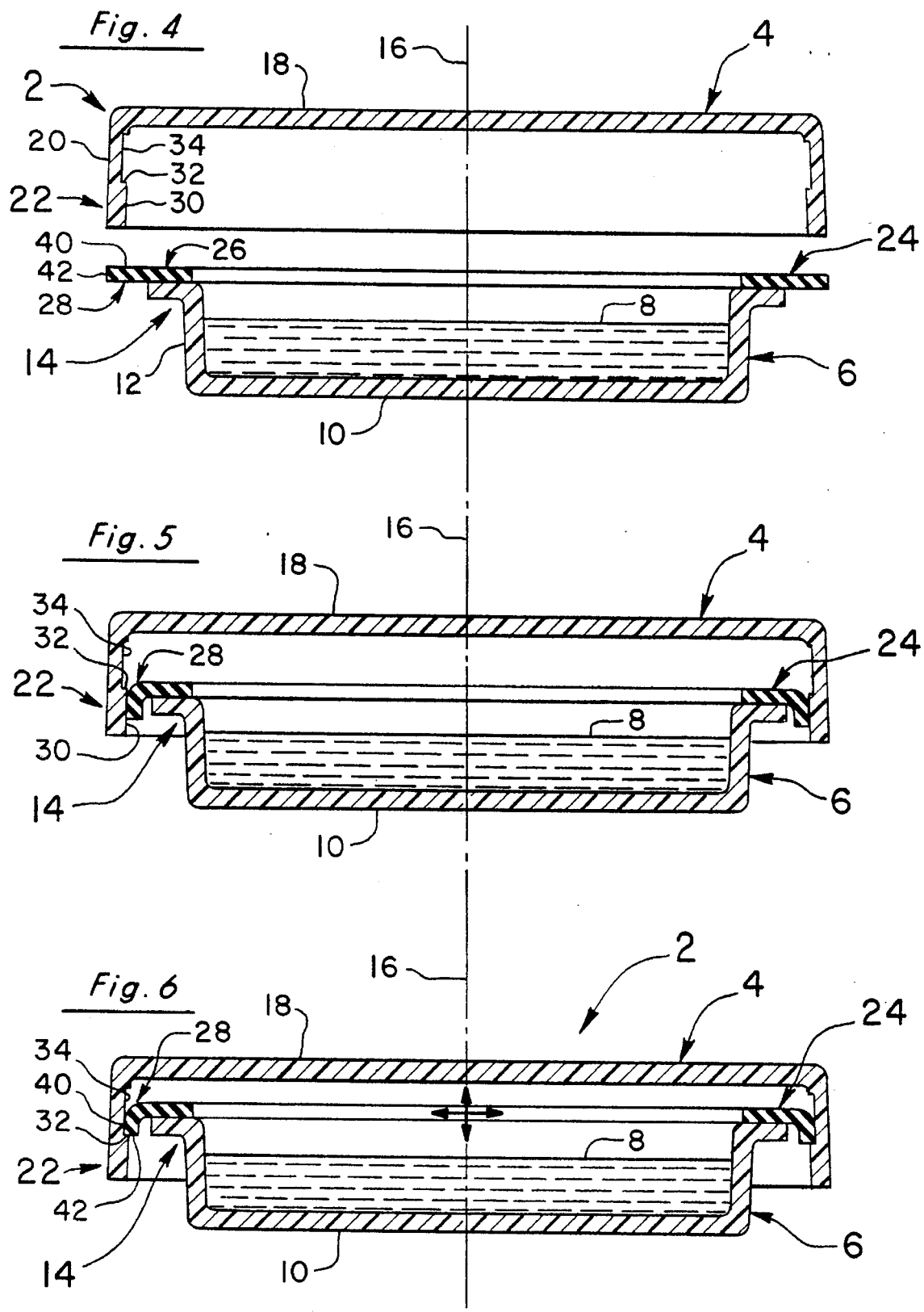

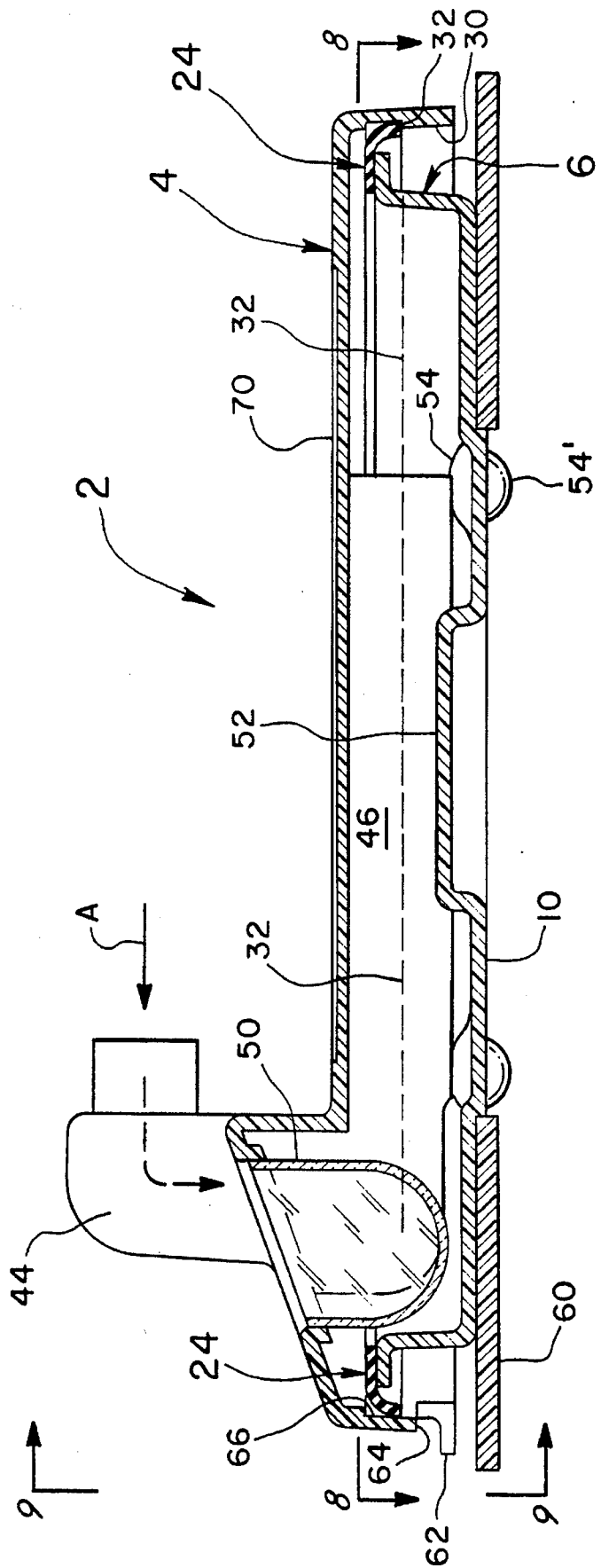

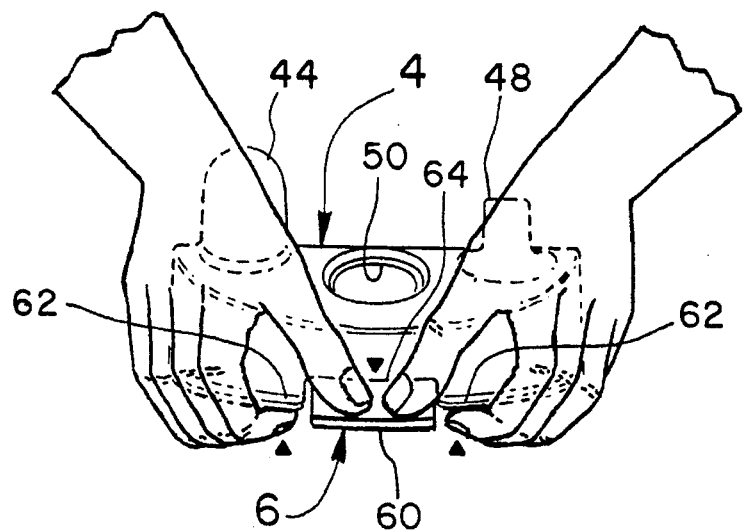
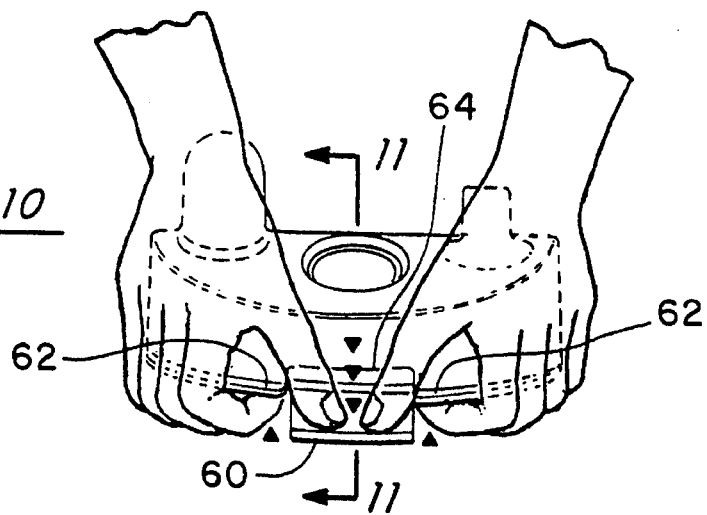
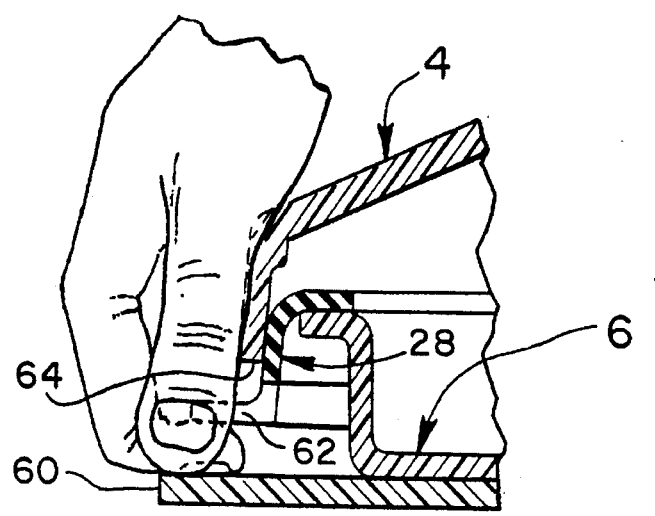

HUMIDIFIER FOR A VENTILATOR

BACKGROUND OF THE INVENTION

1. Field of the Invention

This invention relates to the field of humidifiers for ventilators and other respiratory devices.

2. Discussion of the Background

Humidifiers are commonly used with ventilators and other respiratory devices to add humidity to the air being supplied to a patient. Early humidifying arrangements were simply bottles filled with water with air inlets and outlets. Later arrangements became more sophisticated but still presented many of the same fundamental problems as the earlier bottle ones.

More specifically, prior humidifying units as typified by the early bottle arrangements are somewhat clumsy to use and difficult to clean. Additionally, such units are commonly connected to the ventilator or other respiratory device by a flexible hose. The hose then presents one more item that must be purchased and cleaned. It also takes up valuable space on the night stand or other support structure where space is normally at a premium. This is particularly true in current applications where ventilators are being widely used in home environments to treat sleep apnea. In such environments, the dangling hose between the ventilator and humidifier can easily be accidentally snagged or struck by the patient as he or she manipulates the various controls or moves the unit. The same is true even for hospital environments. The connecting hose is also an additional part that must be disconnected from both the ventilator and humidifier to be periodically cleaned and, like bottles, it is often difficult to properly clean without special brushes or techniques. Such hoses can also be cut or torn in use.

In contrast to the above, the humidifier of the present invention is of the type that has a completely separable top and bottom. It is then much easier and more convenient to reach and clean all parts of the humidifier. Further, the separated top and bottom can even be simply placed in a conventional dishwasher if desired. This ease of cleaning encourages the patient to do so and greatly adds to the safe and sanitary use of the humidifier. Once cleaned, the top and bottom can be easily and quickly assembled using the unique structure and sealing arrangement of the present invention. This sealing arrangement not only gives the patient an audible and tactile signal it is properly engaged but also provides a positive retaining structure to hold the top and bottom together under the elevated air pressure supplied by the ventilator. An attaching arrangement is also provided wherein the ventilator can be easily and quickly attached to the top of the humidifier in a predetermined, fixed position without any intervening, flexible hose.

SUMMARY OF THE INVENTION

This invention involves a sealing and retaining arrangement for a humidifier with separable top and bottom members. It also involves an attaching arrangement for rigidly connecting a ventilator or other respiratory device to the top of the humidifier in a predetermined, fixed position.

The sealing and retaining arrangement is designed for use between separable top and bottom members of a humidifier. The top and bottom are made of relatively rigid material and have overlapping or telescoping portions. A flexible, resilient seal is provided to extend between the telescoping portions to create the seal. It also serves to positively retain the top and bottom together. In the preferred embodiment, the seal has a lip extending about and outwardly of the bottom reservoir member of the humidifier. The top cover member then has an inwardly facing surface with a step or ledge in it. In use, the top cover member is manually placed over the bottom reservoir member and moved downwardly. In doing so, the protruding lip of the seal first contacts and wipes along the surface section below the step. As the top continues to be lowered, the resilient lip snaps outwardly over the step or ledge to strike and sealingly engage the surface section above the step. This snapping action creates a signal that can be both audibly heard and tactually felt by the patient indicating that the top has been properly engaged on the bottom. The top can then be lowered farther if denied. In any case, the lip seal performs the additional function with the step or ledge of positively retaining the top on the bottom while in use. That is, once the resilient lip has snapped outwardly over the step or ledge, any force of the elevated air pressure within the humidifier tending to separate the top and bottom will cause the lip to firmly engage or abut the step or ledge. This will thus serve to positively retain the top on the bottom against any such forces.

The attaching arrangement of the present invention is designed to rigidly connect the ventilator or other respiratory device to the top of the humidifier. This is accomplished by rigidly coupling the air outlet of the ventilator directly to the air inlet of the humidifier without any intervening, flexible hose. The resulting combination is a compact, stable attachment of the ventilator and the humidifier.

BRIEF DESCRIPTION OF THE DRAWINGS

FIG. 4 is a cross-sectional view taken generally along line 4—4 of FIG. 3 of the top cover member and bottom reservoir member of the humidifier.

FIGS. 5 and 6 in conjunction with FIG. 4 sequentially illustrate how the top cover member is manually placed over the bottom reservoir member of the humidifier.

FIG. 7 is a sectional view taken generally along line 7—7 of FIGS. 3 and 8 illustrating the humidifier in its assembled position with the top cover member sealingly engaging and retained on the bottom reservoir member.

FIG. 9 is a view taken generally along line 9—9 of FIG. 7 illustrating how the top and bottom members of the humidifier can be gripped to manually separate them.

FIG. 10 is a view similar to FIG. 9 illustrating how the top and bottom members can be initially pried apart.

FIG. 11 is a view taken along line 11—11 of FIG. 10.

DETAILED DESCRIPTION OF PREFERRED EMBODIMENTS

Figure 1:
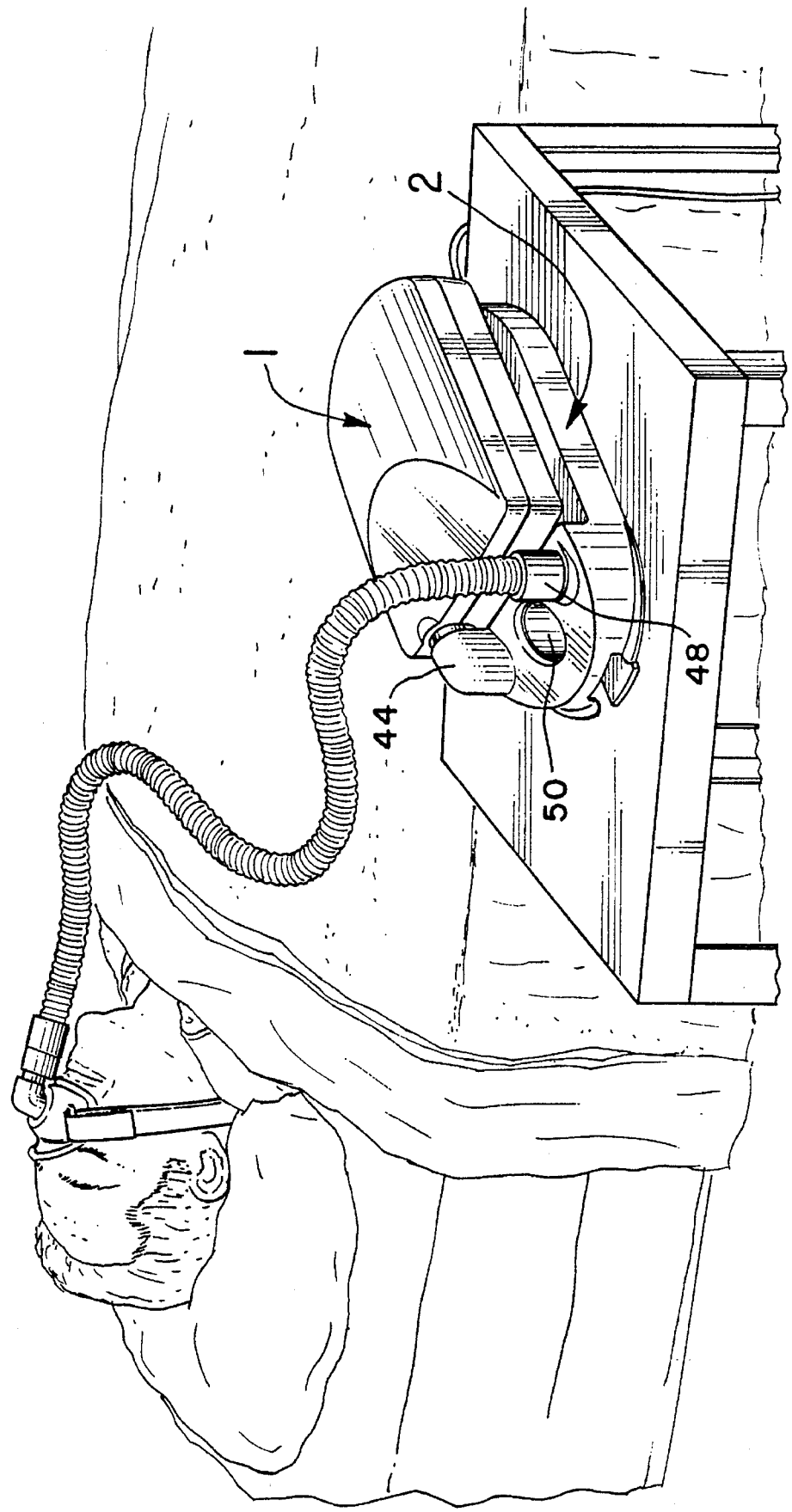
FIG. 1 is a perspective view of the stacked ventilator and humidifier unit of the present invention shown in use supplying humidified air under pressure to a patient.
Figure 2:
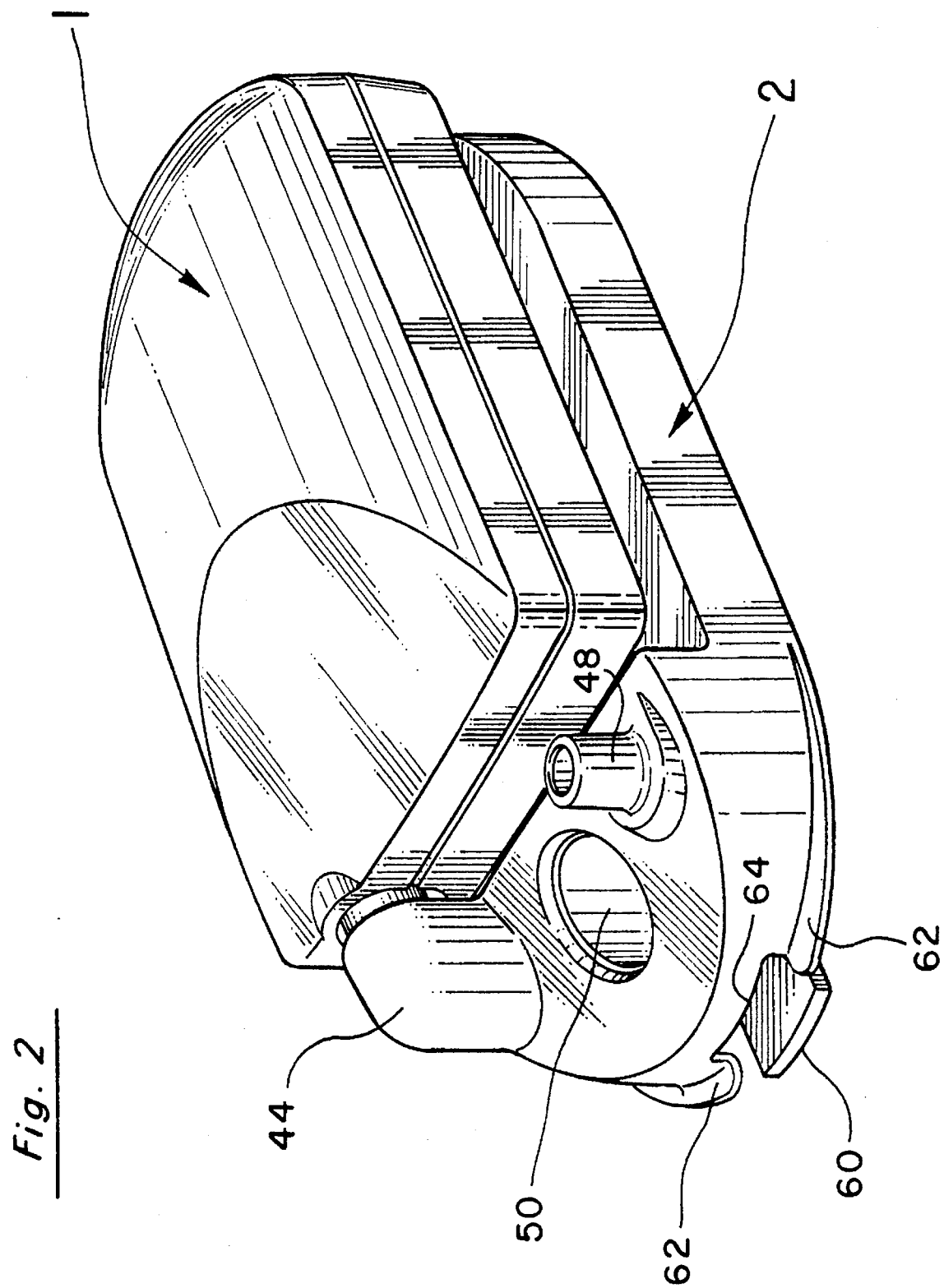
FIG. 2 is an enlarged, perspective view of the ventilator and humidifier unit of the present invention.
Figure 3:
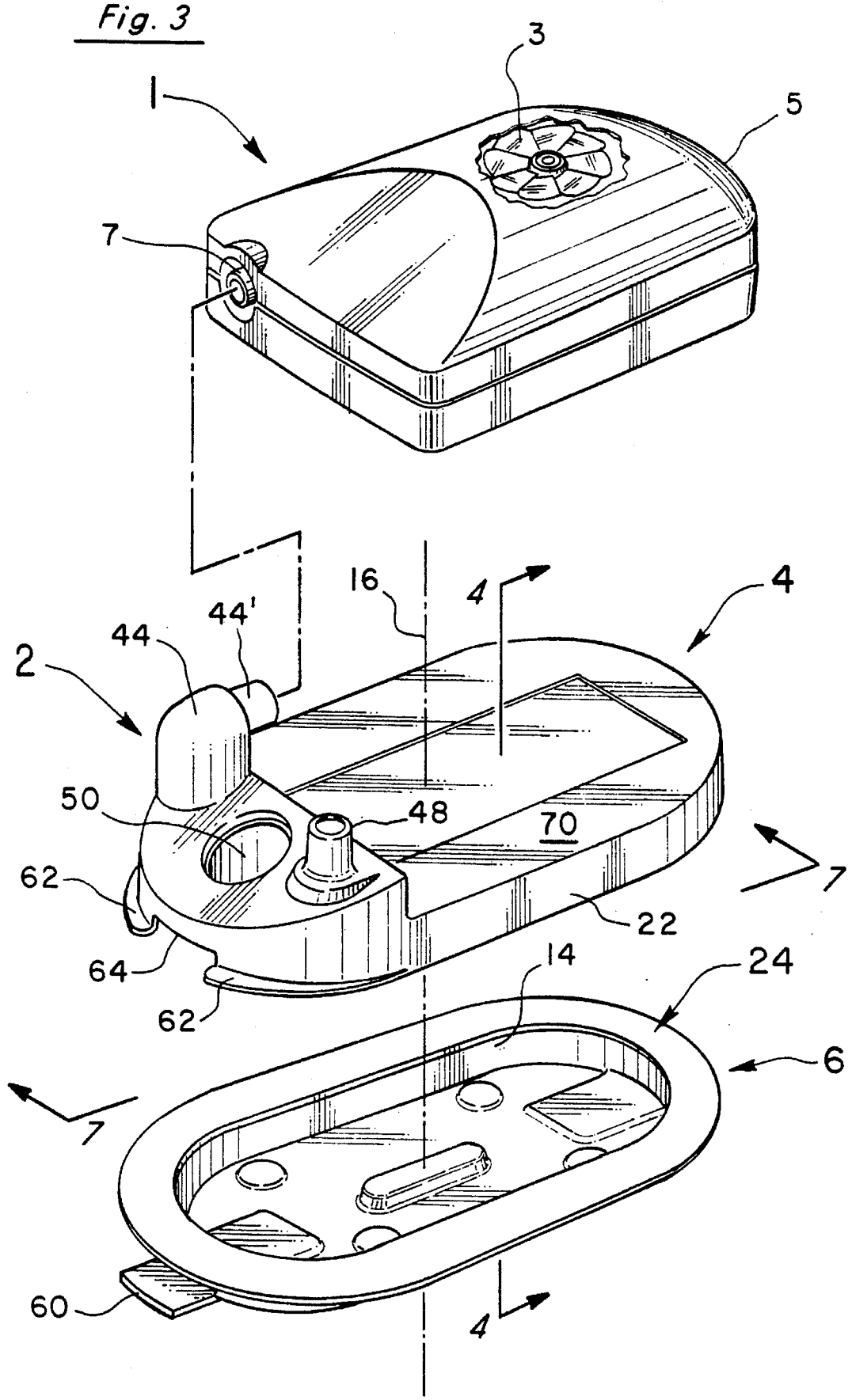
FIG. 3 is a partially exploded view of the ventilator and humidifier.

The sealing, retaining, and attaching arrangements of the present invention as best seen in FIGS. 1–3 have been primarily designed for use in a stackable combination of a ventilator 1 and a humidifier 2. The ventilator 1 (see FIG. 3) is a small, compact unit with a variable speed fan 3 or similar means for generating air flow at pressures above atmospheric. In use, atmospheric air enters through vents in the back 5 of the ventilator 1 and exits under pressure through the outlet 7. For clarity and simplicity, the term ventilator is used herein to include any and all respiratory devices (including respirators) for generating air flow for use by a patient.

Sealing Arrangement

The humidifier 2 as illustrated in the exploded view of FIG. 3 includes separable top and bottom members 4 and 6. Both members 4 and 6 are made of relatively rigid or hard plastic or other material with the top member 4 serving as a separable cover for the bottom member 6. The bottom member 6 as best seen in FIGS. 3–6 serves as a reservoir for holding water 8 and includes a bottom wall 10 (see FIG. 4) and surrounding side wall 12. The side wall 12 extends upwardly from and about the bottom wall 10 to form therewith the reservoir for holding the water 8. The side wall 12 as shown has an upper portion 14 spaced from the bottom wall 10 and extending about the central axis 16. As also illustrated in FIG. 4, the separable top member 4 has a top wall 18 and surrounding side wall 20 extending downwardly from and about the top wall 18. The side wall 20 includes the lower portion 22 which is spaced from the top wall 18 and extends about the axis 16.

In the preferred embodiment, the bottom reservoir member 6 has a resilient, flexible seal 24 which is preferably annular as shown in FIG. 3. Additionally, like the upper and lower portions 14 and 22 of the top and bottom members 4 and 6, the seal 24 also preferably extends substantially elliptically or non-circularly about the axis 16. The seal 24 (see FIG. 4) includes a first or inner section 26 attached (e.g., glued) to the upper portion 14 of the bottom reservoir member 6. The remaining or outer section 28 of the seal 24 extends outwardly of and about the axis 16 and the upper portion 14 to form a protruding lip.

As been seen in FIGS. 4–6, the portions 14 and 22 of the top and bottom members 4 and 6 are concentrically shaped and dimensioned to telescope over each other. In this manner, the patient can manually move the top member 4 along the axis 16 from the separated position of FIG. 4 to the first, telescoping or overlapping position of FIG. 6. In doing so as illustrated in FIG. 5, the lip section 28 of the seal 24 contacts and wipes along the lower surface 30 of the portion 22. Thereafter and as the top cover member 4 is moved to the first, telescoping position of FIG. 6, the outer, lip section 28 of the resilient seal 24 snaps from contact with the surface section 30 over the step or ledge 32 to strike the upper surface section 34. This snapping action creates a signal to the user that the top cover member 4 has been moved downwardly far enough to reach the first, telescoping position of FIG. 6. This snapping action can be both audibly heard and tactually felt by the patient.

In this regard as best seen in FIG. 4, the inner surface of 30, 32, and 34 of the cover member 4 includes the first and second sections 30 and 34. These sections 30 and 34 are spaced from each other along the axis 16. Additionally, these sections 30 and 34 are parallel to one another and to the axis 16 and are spaced different distances from the axis 16. The third section or connecting step or ledge 32 then extends outwardly of the axis 16 and substantially perpendicularly between the surface sections 30 and 34. As discussed above, the upper and lower portions 14 and 22 of the top and bottom 4 and 6 are concentrically shaped and dimensioned so that the top 4 and bottom 6 can be telescoped over one another to the overlapping position of FIG. 6. In this position, the upper and lower portions 14 and 22 are concentrically spaced from each other a first distance to form a gap or space. The flexed lip seal 28 then fills this gap.

More specifically, the outer or lip section 28 of seal 24 extends outwardly in its relaxed state of FIG. 4 for a distance from portion 14 greater than the gap. The outward extent of the relaxed lip 28 from the axis 16 is also greater than the spacing of either of the surface sections 30 and 34 from the axis 16. Consequently, the outer lip section 28 of the seal 24 is flexed downwardly and wipes along the first surface 30 (see FIG. 5) in the direction of axis 16 as the patient manually moves the top 4 downwardly over the bottom 6. Thereafter as the patient continues to move the top 4 downwardly to the position of FIG. 6, the lip 28 resiliently snaps outwardly over the step or ledge 32 to strike and sealingly engage the outer surface section 34. In this first, telescoping position of FIG. 6, the substantially perpendicular surfaces 40 and 42 of the lip 28 respectively abut and seal against the substantially perpendicular surfaces 34 and 32 of the top 4.

Figure 8:
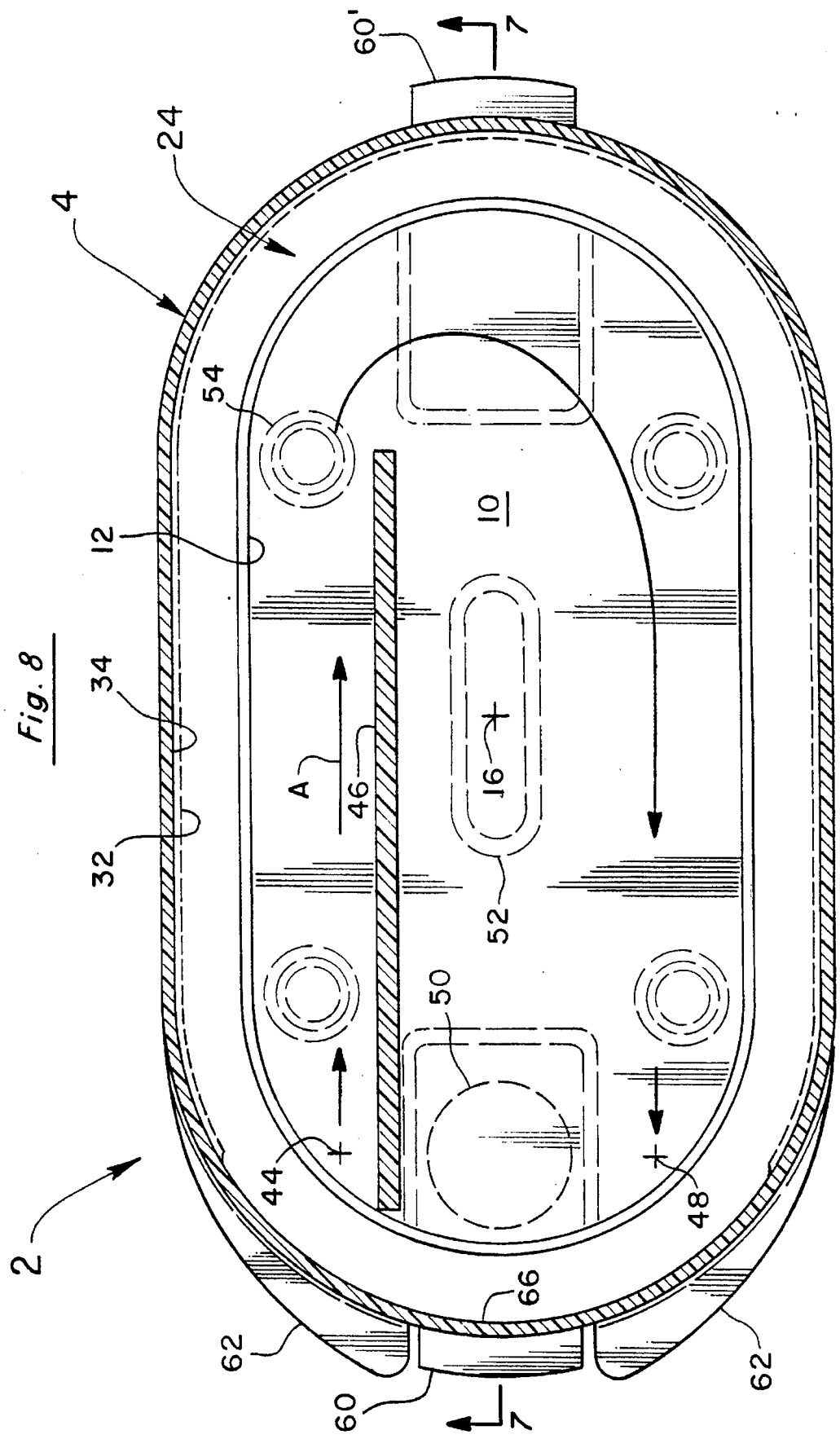
FIG. 8 is a sectional view taken along line 8—8 of FIG. 7.

The humidifier 2 of the present invention has the very desirable feature that the top cover member 4 and bottom reservoir member 6 can be completely separated. It is then much easier and more convenient to reach and thoroughly clean all parts of the humidifier 2. Further, the separated top 4 and bottom 6 can even be simply placed in a conventional dishwasher if desired. This ease of cleaning encourages the patient to do so and greatly adds to the safe and sanitary operation of the humidifier 2. Once cleaned and refilled with water, the humidifier 2 with the separated top 4 and bottom 6 can be easily and quickly assembled to the position of FIG. 6. Member 52 in FIGS. 7 and 8 is a depth gauge wherein water is added (e.g., 11 ounces) until it just covers the top of member 52. This is intended to be enough water with reserve to last through one night's use. In this assembled position (see FIGS. 7 and 8), air A under pressure enters the humidifier 2 through air inlet 44 where it is directed downwardly into the body of the humidifier 2 (FIG. 7). As shown in FIG. 8, the air A then flows around the divider 46 and exits through the outlet 48 and onto the patient (see also FIGS. 1–3). The clear plastic cup 50 in FIGS. 1–3 and 7 is a sight glass through which the patient can visually view and monitor the depth of water in the bottom reservoir member 6. Indentions 54 in the bottom wall 10 of the member 6 are merely recesses to receive the rubber, support feet 54'.

Retaining Arrangement

Referring again to FIG. 6 and with the humidifier 2 under operating air pressure, the top and bottom members 4 and 6 are biased apart by the vertical force components of the pressurized air. That is, the force of the air under pressure passing through the humidifier 2 tends to separate or move the top 4 and bottom 6 apart. To control this as illustrated in FIG. 6, the humidifier 2 is provided with a positive retaining means to hold the top 4 on the bottom 6 against the separating forces of the air pressure.

In the preferred embodiment, this retaining is accomplished by operation of the segment or surface 42 of the lip seal 28 abutting the step or ledge 32 of the top 4. More specifically, as the pressure in the humidifier 2 increases to the point it tends to separate the top 4 and bottom 6, the surface 42 of lip seal 28 engages or abuts the step or ledge 32 of the top 4 to counter and effectively nullify the separating force of the air pressure. The top 4 and bottom 6 are thus safely and positively retained on one another.

To overcome this retaining arrangement in order to separate the top 4 and bottom 6 for cleaning or to add water, a prying arrangement is provided. As best seen in FIGS. 9–11, the prying arrangement includes a push plate 60 on the bottom member 6 and opposing flanges 62 on the top member 4. The flanges 62 are separated by a notch 64 wherein the push plate 60 is aligned with the notch 64 and substantially straddled by the flanges 62 (see FIGS. 9 and 10). In operation, the patient can grip the prying arrangement as shown with his or her thumbs on the push plate 60 in the cut-out space provided by the notch 64 and fingers of each hand respectively on the flanges 62. By applying opposing forces, the top 4 and bottom 6 can be pried or peeled apart. In doing so as best seen in FIG. 11, the patient can position his or her fingers on the outwardly protruding flanges 62 so the descending lip seal 28 will pass by the fingers and not interfere with the separating operation.

To facilitate the prying or separating of the top 4 and bottom 6, the retaining step or ledge 32 is designed to extend only partially about the central axis 16 (see again FIG. 8). Consequently, the remainder 66 (see the left side of FIG. 8) of the inner surface of the top 4 is smooth and has no step or ledge 32. The flanges 62 and notch 64 are then preferably oriented at the end of the top 4 outwardly of this additional, smooth surface 66 (see FIGS. 7 and 8). In this manner and to facilitate the initial prying or separating maneuver of FIGS. 9 and 10, the patient does not have to work directly against the retaining force of an abutting lip 28 and ledge 32. Rather, the top 4 and bottom 6 can be initially separated or peeled apart in the manner of FIGS. 9–11 and the peeling process continued to fully separate the top 4 and bottom 6 using leverage gained by the initial separation of FIGS. 9–11. For the convenience of the user, the bottom 6 as shown is symmetrical and has an additional push plate 60' (see FIG. 8) on its other end so the top 4 can be oriented in either direction on the bottom 6.

Figure 12:
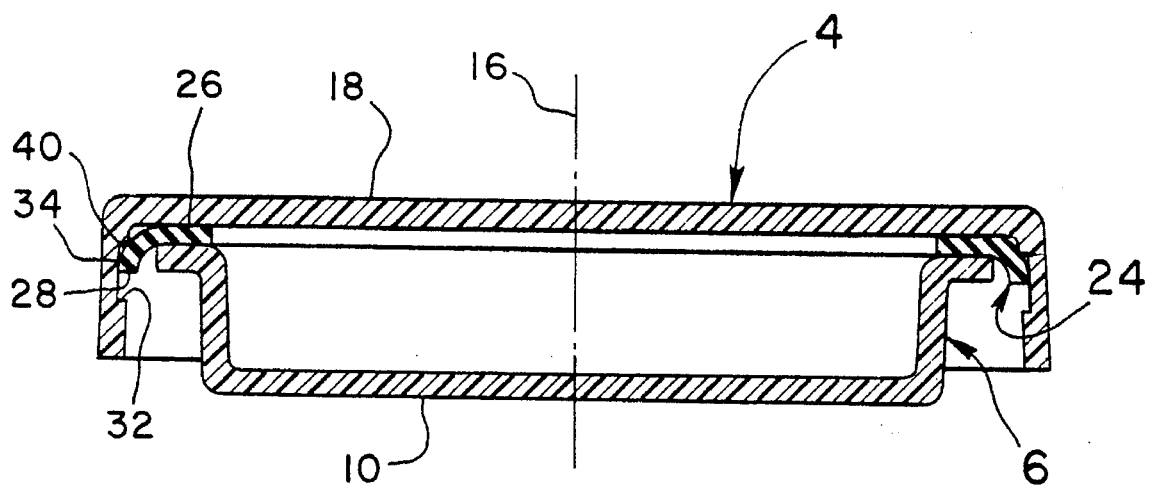
FIG. 12 is a sectional view similar to FIG. 6 showing the top cover member in a lowered position contacting the seal on the bottom reservoir member.
Figure 13:
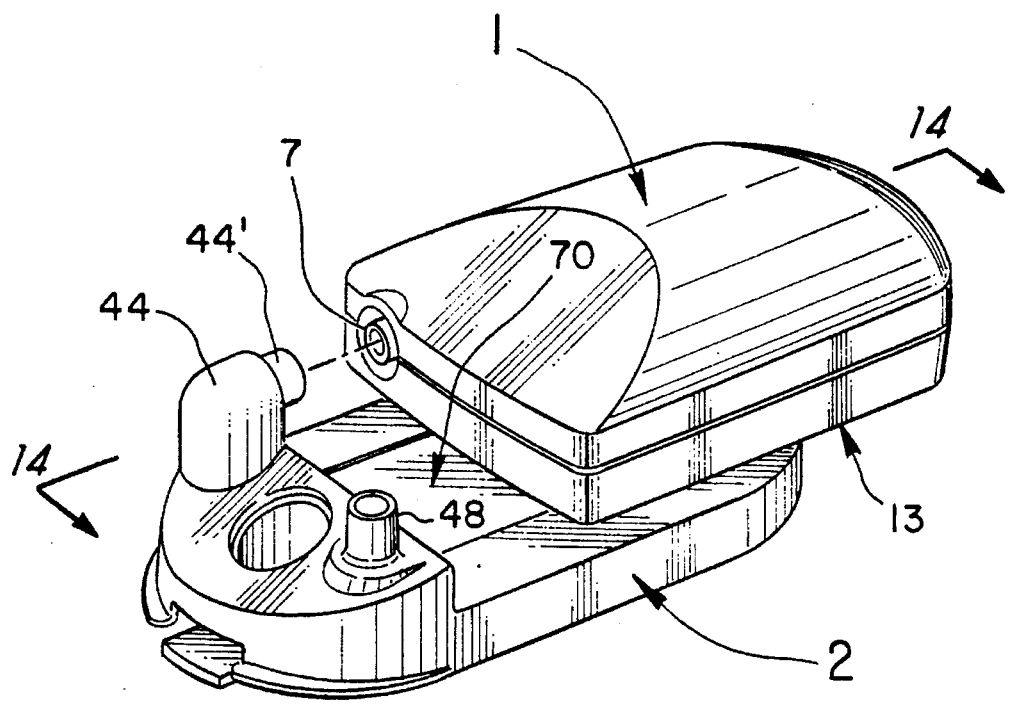
FIG. 13 is a perspective view of the separated ventilator and humidifier.

FIG. 12 corresponds to FIG. 6 and illustrates an alternate and preferred operation of the humidifier 2. In it, the top 4 is moved downwardly beyond the first, telescoping position of FIG. 6 to a second, telescoping position in which the top wall 18 of top 4 actually abuts the inner section 26 of the seal 24. To some extent, this is a manufacturing expedient as it is difficult to mold or manufacture the lip 28 and ledge 32 to precisely abut one another around the axis 16 in the fashion of FIG. 6. Consequently, the preferred manner of manufacture is to dimension the top 4, bottom 6, and seal 24 so that the top 4 can be moved past the first, telescoping position of FIG. 6 to the second, telescoping position of FIG. 12. In the second, telescoping position of FIG. 12, the first or outer surface 40 of lip seal 28 as in FIG. 6 is biased or flexed outwardly and sealingly engages the surface section 34 but with the lip 28 spaced from the retaining ledge 32. In operation as air pressure is initially applied to the interior of the humidifier 2, the force of the flexed lip 28 against the surface 34 is preferably enough to hold the top 4 on the bottom 6 in the position of FIG. 12. Thereafter, as the air pressure may increase (e.g., from 2 centimeters of water to 20, 30, or more), it may become sufficient to move the top 4 and bottom 6 apart from the position of FIG. 12 to that of FIG. 6. However, at the position of FIG. 6, the surface 42 of lip seal 28 will abut the retaining ledge 32 and serve to positively retain the top 4 on the bottom 6 in a safe and reliable manner.

Attaching Arrangement

In the preferred embodiment, the ventilator 1 is removably attached atop the underlying humidifier 2 in a predetermined, fixed position. This is accomplished as illustrated in FIGS. 13–16 by rigidly coupling the air outlet 7 of the ventilator 1 directly to the air inlet 44 of the humidifier 2. This is done without any intervening, flexible hose as is common in the industry. No such additional, intervening hose need then be purchased or cleaned and cannot be struck or otherwise snagged by the patient. Rather, the resulting combination is a compact, stable attachment of the ventilator 1 to the humidifier 2.

Figure 14:
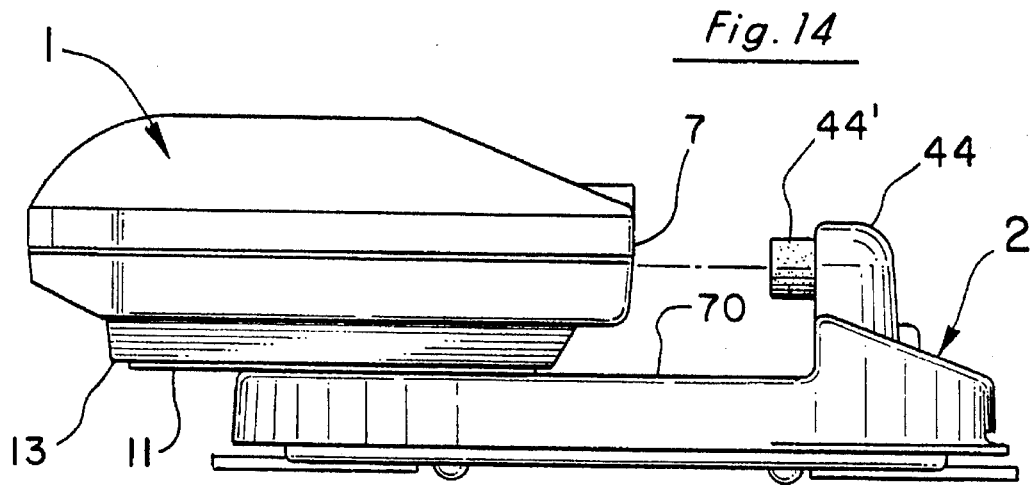
FIG. 14 is a view taken along line 14—14 of FIG. 13.
Figure 15:
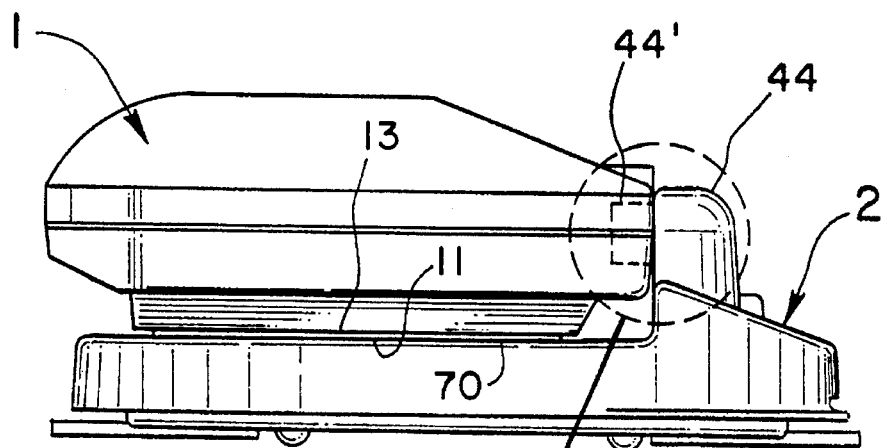
FIG. 15 is a view of the ventilator as it is attached to and atop the humidifier.
Figure 16:
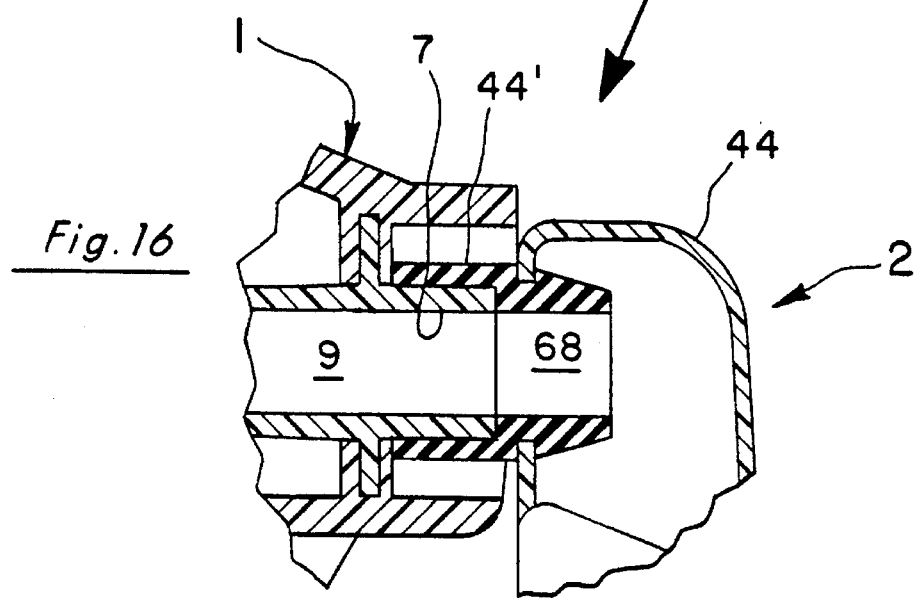
FIG. 16 is an enlarged view of the circled area of FIG. 15 showing the connection between the air outlet of the ventilator and the air inlet of the humidifier.

In this regard, the ventilator 1 and humidifier 2 are rigidly coupled together in the preferred embodiment by the sliding male-female connection 7 on the ventilator 1 and seal member 44' on the humidifier 2. Seal member 44' is an extension of and forms part of the air inlet means 44 for the humidifier 2. In operation, as shown in FIGS. 14–16, the ventilator 1 and humidifier 2 are slid together until the air outlet means 7 of the ventilator 1 is firmly received in the seal member 44' of the air inlet means 44 of the humidifier 2. In this manner, the respective male-female members 7 and 44' not only serve to define air flow passages 9 and 68 (see FIG. 16) but also serve as removable attaching means to maintain the ventilator 1 in a predetermined, fixed position on the humidifier 2. Thus, the act of placing the flow passages 9 and 68 in fluid communications with each other sealing engages the air outlet 7 and air inlet 44 and at the same time, affixes the ventilator 1 in a stacked position atop the humidifier 2.

The bottom of the ventilator 1 as shown in FIGS. 14 and 15 preferably has one or more strips 11 of non-skid material (e.g., rubber) to frictionally engage the top surface 70 of the humidifier 2. These strips 11 serve to inhibit relative sliding between the horizontal surfaces 13 and 70 of the ventilator 1 and humidifier 2. The strips 11 are very thin and their thickness is greatly exaggerated in the drawings for clarity as the substantially horizontal, parallel surfaces 13 and 70 nearly abut one another in the position of FIG. 15. If desired, the surfaces 13 and 70 can rest directly on one another. Additionally, as shown, the bottom 13 of the ventilator 1 and surface section 70 of the humidifier 2 preferably are substantially similar in shape and size so as to form a compact, stable unit.

While several embodiments of the present invention have been shown and described in detail, it is to be understood that various modifications and changes could be made without departing from the scope of the invention. For example, the term ventilator as explained above is used herein to include any and all respiratory devices (including respirators) for generating air flow for use by a patient. Further, the sealing arrangement as well as the retaining and attaching arrangements were described in the preferred embodiments as being on specific members. However, they could be on the other or opposing member. Other equivalents and mirror roles would also be apparent to one skilled in the art.

We claim:

1. A sealing arrangement primarily intended for use in a humidifier for a ventilator, said humidifier having separable, relatively rigid, top and bottom members, said relatively rigid, bottom member being a reservoir for holding water and having a bottom wall and a side wall, said side wall extending upwardly from and about said bottom wall to form therewith said reservoir for holding water, said side wall having an upper portion spaced from the bottom wall and extending about an axis, said separable, relatively rigid, top member of said humidifier being a cover for said bottom reservoir member and having a top wall and a side wall, said side wall extending downwardly from and about said top wall, said side wall of said top cover member having a lower portion spaced from the top wall and extending about said axis, one of said bottom reservoir member and said top cover member further including a resilient, flexible seal, said seal having a first section attached to one of the upper portion of the side wall of the bottom reservoir member and the lower portion of the side wall of the top cover member and extending about said axis, said seal further having a second section extending from the one of the upper portion of the bottom reservoir member and the lower portion of the top cover member to form a protruding lip, said upper portion of the side wall of the bottom reservoir member and said lower portion of the side wall of the top cover member being substantially concentrically shaped and dimensioned wherein said top cover member can be manually moved by a patient along said axis to a first, telescoping position relative to the bottom reservoir member with the respective upper and lower portions of the top cover member and bottom reservoir member overlapping and concentrically spaced a first distance from each other, said second section of said resilient, flexible seal forming said protruding lip having a relaxed state extending from the one of said upper and lower portions for a distance greater than said first distance said upper and lower portions are concentrically spaced from each other wherein said lip contacts and wipes along the other of said upper and lower portions in the direction of said axis as said top cover member is moved by the patient to said first, telescoping position relative to said bottom reservoir member, said lip on the one of said upper and lower portions sealingly engaging the other of said upper and lower portions in said first, telescoping position, and said sealing arrangement further including means for creating a signal to the patient indicating the top cover member has been moved to said first, telescoping and sealing position, said signal creating means including said lip and means for causing said lip to resiliently snap against the other of said upper and lower portions to create said signal when the top cover member has been moved to said first, telescoping and sealing position.

2. The sealing arrangement of claim 1 wherein said signaling means creates an audible signal that can be heard by the patient.

3. The sealing arrangement of claim 1 wherein said signaling means creates a tactile signal that can be felt by the patient.

4. The sealing arrangement of claim 1 wherein said upper and lower portions respectively extend substantially elliptically about said axis.

5. The sealing arrangement of claim 1 wherein said upper and lower portions respectively extend non-circularly about said axis.

6. The sealing arrangement of claim 1 wherein said seal is annularly shaped about said axis.

7. The sealing arrangement of claim 1 wherein said seal extends elliptically about said axis.

8. The sealing arrangement of claim 1 wherein said seal extends non-circularly about said axis.

9. The sealing arrangement of claim 1 wherein said humidifier includes an air inlet means in the top cover member and an air outlet and said ventilator includes means for supplying air under pressure above atmospheric to the air inlet means of said humidifier, said air inlet means of said humidifier including means for removably attaching said ventilator thereto in a predetermined, fixed position.

10. The sealing arrangement of claim 1 further including means for positively retaining said top cover member on said bottom reservoir member.

11. A sealing arrangement primarily intended for use in a humidifier for a ventilator, said humidifier having separable, relatively rigid, top and bottom members, said relatively rigid, bottom member being a reservoir for holding water and having a bottom wall and a side wall, said side wall extending upwardly from and about said bottom wall to form therewith said reservoir for holding water, said side wall having an upper portion spaced from the bottom wall and extending about an axis, said separable, relatively rigid, top member of said humidifier being a cover for said bottom reservoir member and having a top wall and a side wall, said side wall extending downwardly from and about said top wall, said side wall of said top cover member having a lower portion spaced from the top wall and extending about said axis, one of said bottom reservoir member and said top cover member further including a resilient, flexible seal, said seal having a first section attached to one of the upper portion of the side wall of the bottom reservoir member and the lower portion of the side wall of the top cover member and extending about said axis, said seal further having a second section extending from the one of the upper portion of the bottom reservoir member and the lower portion of the top cover member to form a protruding lip, said upper portion of the side wall of the bottom reservoir member and said lower portion of the side wall of the top cover member being substantially concentrically shaped and dimensioned wherein said top cover member can be manually moved by a patient along said axis to a first, telescoping position relative to the bottom reservoir member with the respective upper and lower portions of the top cover member and bottom reservoir member overlapping and concentrically spaced a first distance from each other, said second section of said resilient, flexible seal forming said protruding lip having a relaxed state extending from the one of said upper and lower portions for a distance greater than said first distance said upper and lower portions are concentrically spaced from each other wherein said lip contacts and wipes along the other of said upper and lower portions in the direction of said axis as said top cover member is moved by the patient to said first, telescoping position relative to said bottom reservoir member, said lip on the one of said upper and lower portions sealingly engaging the other of said upper and lower portions in said first, telescoping position, and said sealing arrangement further including means for creating a signal to the patient indicating the top cover member has been moved to said first, telescoping and sealing position wherein the other of said upper and lower portions has a surface with first and second sections spaced from each other along said axis, said first and second sections additionally being spaced different distances from said axis and said surface further including a third section extending outwardly of said axis between said first and second sections to form a step, said lip of said seal contacting and wiping along said first section in the direction of said axis and thereafter sealingly engaging said second section when said top cover member is in said first, telescoping and sealing position.

12. The sealing arrangement of claim 11 wherein said signaling means includes said lip wherein said lip resiliently snaps from contact with said first section over said step to strike the second section of said surface as said top cover member is moved by said patient along said axis to said first sealing position.

13. The sealing arrangement of claim 12 wherein said top cover member telescopes over said bottom reservoir member with the lower portion of said top cover member positioned concentrically outwardly of the upper portion of the bottom reservoir member, the inner section of the seal is attached to the upper portion of the bottom reservoir member and the lip of said seal extends outwardly of the upper portion of said bottom reservoir member, the surface with the three sections is on the lower portion of said top cover member and the first and second sections thereof face inwardly toward said axis with the second section being spaced farther from said axis than said first section wherein said lip resiliently snaps outwardly from contact with said first section over said step to strike the second section of said surface of said top cover member as said top cover member is moved by the patient along said axis to said first sealing position.

14. A sealing arrangement primarily intended for use in a humidifier for a ventilator, said humidifier having separable, relatively rigid top and bottom members, said relatively rigid, bottom member being a reservoir for holding water and having a bottom wall and a side wall, said side wall extending upwardly from and about said bottom wall to form therewith said reservoir for holding water, said side wall having an upper portion spaced from the bottom wall and extending about an axis, said separable, relatively rigid, top member of said humidifier being a cover for said bottom reservoir member and having a top wall and a side wall, said side wall extending downwardly from and about said top wall, said side wall of said top cover member having a lower portion spaced from the top wall and extending about said axis, one of said bottom reservoir member and said top cover member further including a resilient, flexible seal, said seal having a first section attached to one of the upper portion of the side wall of the bottom reservoir member and the lower portion of the side wall of the top cover member and extending about said axis, said seal further having a second section extending from the one of the upper portion of the bottom reservoir member and the lower portion of the top cover member to form a protruding lip, said upper portion of the side wall of the bottom reservoir member and said lower portion of the side wall of the top cover member being substantially concentrically shaped and dimensioned wherein said top cover member can be manually moved by a patient along said axis to a first, telescoping position relative to the bottom reservoir member with the respective upper and lower portions of the top cover member and bottom reservoir member overlapping and concentrically spaced a first distance from each other, said second section of said resilient, flexible seal forming said protruding lip having a relaxed state extending from the one of said upper and lower portions for a distance greater than said first distance said upper and lower portions are concentrically spaced from each other wherein said lip contacts and wipes along the other of said upper and lower portions in the direction of said axis as said top cover member is moved by the patient to said first, telescoping position relative to said bottom reservoir member, said lip on the one of said upper and lower portions sealingly engaging the other of said upper and lower portions in said first, telescoping position, and said sealing arrangement further including means for creating a signal to the patient indicating the top cover member has been moved to said first, telescoping and sealing position and means for positively retaining said top cover member on said bottom reservoir member wherein the other of said upper and lower portions has a surface with first and second sections spaced from each other along said axis, said first and second sections additionally being spaced different distances from said axis and said surface further including a third section extending outwardly of said axis between said first and second sections to form a ledge, said retaining means including said ledge wherein said lip abuts said ledge to positively retain said top cover member on said bottom reservoir member.

15. The sealing arrangement of claim 14 wherein said first and second surface sections are substantially parallel to each other and to said axis and said third surface is substantially perpendicular to said first and second surface sections and to said axis.

16. A sealing arrangement primarily intended for use in a humidifier for a ventilator, said humidifier having separable, relatively rigid, top and bottom members, said relatively rigid, bottom member being a reservoir for holding water and having a bottom wall and a side wall, said side wall extending upwardly from and about said bottom wall to form therewith said reservoir for holding water, said side wall having an upper portion spaced from the bottom wall and extending about an axis, said separable, relatively rigid, top member of said humidifier being a cover for said bottom reservoir member and having a top wall and a side wall, said side wall extending downwardly from and about said top wall, said side wall of said top cover member having a lower portion spaced from the top wall and extending about said axis, one of said bottom reservoir member and said top cover member further including a resilient, flexible seal, said seal having a first section attached to one of the upper portion of the side wall of the bottom reservoir member add the lower portion of the side wall of the top cover member and extending about said axis, said seal further having a second section extending from the one of the upper portion of the bottom reservoir member and the lower portion of the top cover member to form a protruding lip, said upper portion of the side wall of the bottom reservoir member and said lower portion of the side wall of the top cover member being substantially concentrically shaped and dimensioned wherein said top cover member can be manually moved by a patient along said axis to a first, telescoping position relative to the bottom reservoir member with the respective upper and lower portions of the top cover member and bottom reservoir member overlapping and concentrically spaced a first distance from each other, said second section of said resilient, flexible seal forming said protruding lip having a relaxed state extending from the one of said upper and lower portions for a distance greater than said first distance said upper and lower portions are concentrically spaced from each other wherein said lip contacts and wipes along the other of said upper and lower portions in the direction of said axis as said top cover member is moved by the patient to said first, telescoping position relative to said bottom reservoir member, said lip on the one of said upper and lower portions sealingly engaging the other of said upper and lower portions in said first, telescoping position, and said sealing arrangement further including means for creating a signal to the patient indicating the top cover member has been moved to said first, telescoping and sealing position wherein said humidifier has an air inlet and an air outlet and said ventilator includes means for supplying air under pressure above atmospheric to the air inlet of said humidifier, said air under pressure in said humidifier creating a force tending to move said top cover member and said bottom reservoir member apart and said sealing arrangement further including means for positively retaining said top cover member on said bottom reservoir member against the force of the air under pressure tending to move the top cover member and bottom reservoir member apart.

17. A retaining arrangement primarily intended for use in a humidifier for a ventilator, said humidifier having separable, relatively rigid, top and bottom members, said relatively rigid, bottom member being a reservoir for holding water and having a bottom wall and a side wall, said side wall extending upwardly from and about said bottom wall to form therewith said reservoir for holding water, said side wall having an upper portion spaced from the bottom wall and extending about an axis, said separable, relatively rigid, top member of said humidifier being a cover for said bottom reservoir member and having a top wall and a side wall, said side wall extending downwardly from and about said top wall, said side wall of said top cover member having a lower portion spaced from the top wall and extending about said axis, one of said bottom reservoir member and said top cover member further including a resilient, flexible seal, said seal having a first section attached to one of the upper portion of the side wall of the bottom reservoir member and the lower portion of the side wall of the top cover member and extending about said axis, said seal further having a second section extending from the one of the upper portion of the bottom reservoir member and the lower portion of the top cover member to form a protruding lip, said upper portion of the side wall of the bottom reservoir member and said lower portion of the side wall of the top cover member being substantially concentrically shaped and dimensioned wherein said top cover member can be manually moved by a patient along said axis to a first, telescoping position relative to the bottom reservoir member with the respective upper and lower portions of the top cover member and bottom reservoir member overlapping and concentrically spaced a first distance from each other, said second section of said resilient, flexible seal forming said protruding lip having a relaxed state extending from the one of said upper and lower portions for a distance greater than said first distance said upper and lower portions are concentrically spaced from each other wherein said lip contacts and wipes along the other of said upper and lower portions in the direction of said axis as said top cover member is moved by the patient to said first, telescoping position relative to said bottom reservoir member, said lip on the one of said upper and lower portions sealingly engaging the other of said upper and lower portions in said first, telescoping position, and means for positively retaining said top cover member on said bottom reservoir member wherein the other of said upper and lower portions has a surface with first and second sections spaced from each other along said axis, said first and second sections additionally being spaced different distances from said axis and said surface further including a third section extending outwardly of said axis between said first and second sections to form a ledge, said retaining means including said ledge wherein said lip abuts said ledge to positively retain said top cover member on said bottom reservoir member.

18. The retaining arrangement of claim 17 wherein said top cover member telescopes over said bottom reservoir member with the lower portion of said top cover member positioned concentrically outwardly of the upper portion of the bottom reservoir member, the inner section of the seal is attached to the upper portion of the bottom reservoir member and the lip of said seal extends outwardly of the upper portion of said bottom reservoir member, the surface with the three sections is on the lower portion of said top cover member and the first and second sections thereof face inwardly toward said axis with the second section being spaced farther from said axis than said first section wherein said lip resiliently snaps outwardly from contact with said first section over said ledge to strike the second section of said surface of said top cover member as said top cover member is moved by the patient along said axis to said first sealing position.

19. The retaining arrangement of claim 17 wherein said upper and lower portions respectively extend substantially elliptically about said axis.

20. The retaining arrangement of claim 17 wherein said upper and lower portions respectively extend non-circularly about said axis.

21. The retaining arrangement of claim 17 wherein said seal is annularly shaped about said axis.

22. The retaining arrangement of claim 17 wherein said seal extends elliptically about said axis.

23. The retaining arrangement of claim 17 wherein said seal extends non-circularly about said axis.

24. The retaining arrangement of claim 17 wherein said humidifier includes an air inlet means in the top cover member and an air outlet and said ventilator includes means for supplying air under pressure above atmospheric to the air inlet means of said humidifier, said air inlet means of said humidifier including means for removably attaching said ventilator thereto in a predetermined, fixed position.

25. The retaining arrangement of claim 17 further including means for creating a signal to the patient indicating the top cover member has been moved to said first, telescoping position.

26. The retaining arrangement of claim 25 wherein said signaling means creates an audible signal that can be heard by the patient.

27. The retaining arrangement of claim 25 wherein said signaling means creates a tactile signal that can be felt by the patient.

28. The retaining arrangement of claim 17 wherein the lip of said seal has first and second surfaces, said first surface contacting and sealing against said second section of the surface of the other of said upper and lower portions in said first, telescoping position and said second surface of said lip abutting said ledge in said first, telescoping position.

29. The retaining arrangement of claim 28 wherein said top cover member can be further moved by the patient along said axis toward said bottom reservoir member from said first, telescoping position to a second, telescoping position with said first surface of said lip sealingly engaging said second section of the surface of the other of said upper and lower portions and said second surface of said lip spaced from said ledge.

30. The retaining arrangement of claim 29 wherein said humidifier has an air inlet and an air outlet and said ventilator includes means for supplying air under pressure above atmospheric to the air inlet of said humidifier, said air under pressure creating a force tending to move said top cover member and said bottom cover member apart from said second, telescoping position toward said first, telescoping position.

31. The retaining arrangement of claim 29 wherein one of the top wall of said top cover member and the bottom wall of said bottom reservoir member abuts said seal in said second, telescoping position.

32. The retaining arrangement of claim 31 wherein the one of said top and bottom walls abuts the first section of said seal in said second, telescoping position.

33. The retaining arrangement of claim 17 wherein said first and second surface sections are substantially parallel to each other and to said axis and said third surface section is substantially perpendicular to said first and second surface sections and to said axis.

34. The retaining arrangement of claim 33 wherein said ledge extends only partially about said axis.

35. The retaining arrangement of claim 33 wherein said surface of the other of said upper and lower portions with said first, second, and third sections extends only partially about said axis and said other of said upper and lower portions has an additional surface extending substantially the remainder about said axis, said additional surface being substantially smooth.

36. The retaining arrangement of claim 35 wherein the lip of said seal extends about said axis with a segment thereof abutting said ledge in said first, telescoping position and another segment of said lip abutting and sealing against the smooth, additional surface in said first, telescoping position.

37. The retaining arrangement of claim 35 further including a prying arrangement to assist the patient in manually separating the top cover member and the bottom reservoir member from said first, telescoping position, said prying arrangement including a push plate on the bottom reservoir member and flange means on the top cover member, said flange means being positioned about said axis outwardly of said smooth, additional surface when said top cover member and said bottom reservoir member are in said first, telescoping position.

38. The retaining arrangement of claim 37 wherein said flange means extends outwardly of the lower portion of said top cover member.

39. The retaining arrangement of claim 37 wherein said flange means has first and second flanges separated by a notch and said push plate is aligned with said notch and substantially staddled by said first and second flanges when said top cover member and said bottom reservoir member are in said first, telescoping position wherein the patient can grip the prying arrangement with the patient's thumbs on said push plate and the patient's fingers on each hand respectively on said first and second flanges.

* * * * *